(12) United States Patent
Bajgrowicz

(10) Patent No.: US 7,655,614 B2
(45) Date of Patent: Feb. 2, 2010

(54) 3-ISOPROPYL-1-METHYLCYCLOPENTYL DERIVATIVES AND THEIR USE IN FRAGRANCE APPLICATIONS

(75) Inventor: Jerzy A. Bajgrowicz, Zurich (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 10/573,621

(22) PCT Filed: Sep. 29, 2004

(86) PCT No.: PCT/CH2004/000605

§ 371 (c)(1),
(2), (4) Date: Mar. 28, 2006

(87) PCT Pub. No.: WO2005/030915

PCT Pub. Date: Apr. 7, 2005

(65) Prior Publication Data

US 2007/0082837 A1    Apr. 12, 2007

(51) Int. Cl.
*A61Q 13/00* (2006.01)
*C07C 35/06* (2006.01)

(52) U.S. Cl. .............................. 512/8; 512/1; 568/838

(58) Field of Classification Search .................... 512/1, 512/8; 568/838
See application file for complete search history.

(56) References Cited

U.S. PATENT DOCUMENTS 4,234,463 A    11/1980 Sprecker et al.
4,533,492 A    8/1985 Tokarzewski et al.

OTHER PUBLICATIONS

Abramov et at (Zhurnal Obshchei Khimii (1952), 22, 1450-1457).*
International Search Report dated Dec. 10, 2004 for application PCT/CH2004/000605.
Written Opinion of the International Searching Authority for application PCT/CH2004/000605 (Dec. 19, 2004).
Patent Abstracts of Japan; vol. 0151, No. 45 (c-0823), Apr. 12, 1991 & JP 3 024198 A (Takasago International), Feb. 1, 1991; abstract.
P.L. Pickard, et al.: "Ketimines. IV. From Fencholonitrile"; Journal of the American Chemical Society, vol. 74, No. 18; Sep. 20, 1952, pp. 4607-4608; XP002309944; American Chemical Society, Washington DC, US; ISSN: 0002-7863; table III.
F.J. McCarthy, et al.: "Central stimulants. alpha, alpha-Disubstituted 2-piperidinemethanols and 1,1-disubstituted heptahydrooxazolo '3,4-a!pyridines"; Journal of the American Chemical Society, vol. 79, No. 2, Jan. 20, 1957, pp. 472-480; XP002309943; American Chemical Society, Washington, DC, US; ISSN: 0002-7863; Compound 41A.
G. Rüedi, et al.: "An unusual domino retro-ene-Conia reaction: region- and stereoselective one-carbon ring expansion of fenchol derivatives"; Helvetica Chimica Acta, vol. 87, No. 8, Aug. 27, 2004, pp. 1990-2021; XP002309865; Verlag Helvetica Chimica Acta, Basel, CH; compounds 9, (E)-17, (Z)-17, 20.
Julius v. Braun and Anni Jacob. Ber. 66B, 1461-4 (1933). See enclosed document, col. 138, line 79—col. 139, line 20.

* cited by examiner

*Primary Examiner*—Porfirio Nazario Gonzalez
(74) *Attorney, Agent, or Firm*—Norris McLaughlin & Marcus, PA

(57) ABSTRACT

This invention relates to 3-isopropyl-1-methylcyclopentyl derivatives and their use in fragrance applications.

8 Claims, No Drawings

3-ISOPROPYL-1-METHYLCYCLOPENTYL DERIVATIVES AND THEIR USE IN FRAGRANCE APPLICATIONS

This application is an application filed under 35 USC 371 based on PCT/CH2004/000605.

The present invention relates to 3-isopropyl-1-methylcyclopentyl derivatives, having floral, fruity and woody odour notes, and their use as fragrances. This invention relates furthermore to a method for their production and to fragrance compositions comprising them.

In the fragrance industry there is a constant demand for new compounds that enhance or improve on odour notes, or impart new odour notes.

It has now been found that certain 3-isopropyl-1-methylcyclopentyl derivatives have much sought-after floral, fruity and woody odour notes, and they are relatively simple and easy to prepare starting from readily-available cheap and naturally-available starting materials.

Accordingly, the present invention refers in one of its aspects to the use of a compound of formula I as fragrance

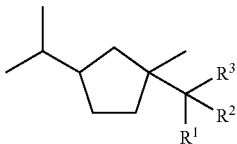

I wherein $R^1$ is hydrogen; or $R^1$ and $R^2$ are independently $C_{2-8}$ alkyl, preferably $C_{2-4}$, e.g. ethyl, $C_{2-8}$ alkenyl, $C_{3-8}$ cycloalkyl, $C_{3-8}$ cycloalkyl substituted with at least one $C_{1-3}$ alkyl, such as methylcyclopentyl, aryl, such as phenyl, or aryl group substituted with at least one $C_{1-3}$ alkyl group, such as tolyl;

$R^3$ is hydroxy, $C_{1-8}$ alkoxy, e.g. methoxy, ethoxy and isopropoxy, $C_{3-8}$ cycloalkoxy, $C_{2-5}$ alkoxymethyloxy, e.g. methoxymethyloxy, ethoxymethyloxy, aryloxy, e.g. phenoxy, or aryloxy wherein the aromatic ring is substituted with $C_{1-3}$ alkyl; or $R^2$ and $R^3$ form together with the carbon atom to which they are attached a carbonyl group.

Particularly preferred compounds of formula I are (1R,cis)-1-ethoxymethoxymethyl-3-isopropyl-1-methylcyclopentane, 1-[(1R,cis)-3-isopropyl-1-methylcyclopentyl]propan-1-one, 1-[(1S,cis)-3-isopropyl-1-methylcyclopentyl] propan-1-one, 1-[(1R,cis)-3-isopropyl-1-methylcyclopentyl] pentan-1-one, 1-[(1R,cis)-3-isopropyl-1-methylcyclopentyl] propan-1-ol, 1-[(1S,cis)-3-isopropyl-1-methylcyclopentyl] propan-1-ol, 1-[(1R,cis)-3-isopropyl-1-methylcyclopentyl] pentan-1-ol, 2-[(1R,cis)-3-isopropyl-1-methylcyclopentyl] propan-2-ol, 2-[(1S,cis)-3-isopropyl-1-methylcyclopentyl] propan-2-ol, 2-[(1R,cis)-3-isopropyl-1-methylcyclopentyl] butan-2-ol, 2-[(1S,cis)-3-isopropyl-1-methylcyclopentyl] butan-2-ol, 2-[(1R,cis)-3-isopropyl-1-methylcyclopentyl] pent-3-en-2-ol, 3-[(1R,cis)-3-isopropyl-1-methylcyclopentyl]pentan-3-ol, and 1-[(1R,cis)-3-isopropyl-1-methylcyclopentyl]butan-1-ol.

The compounds of formula I may comprise at least two chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC or by stereoselective synthesis.

It is known by the skilled man that enantiomers are similar in their physical properties, but may differ, for example, in their physiological properties and organoleptic properties.

Thus, in a further aspect, the present invention refers to the use of a compound of formula I enriched in one of its enantiomers of formula Ia (i.e. (1R,cis)-) or formula Ib (i.e. (1S,cis)-)

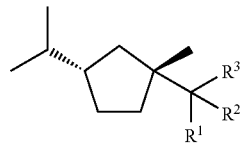

Ia

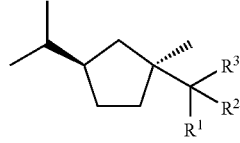

Ib wherein $R^1$, $R^2$ and $R^3$ have the same meaning as above.

It has been found that the odour threshold of certain compounds of formula Ia is on an average two times lower than that of the corresponding enantiomer. Accordingly, compounds of formula I enriched in its corresponding (1R,cis) enantiomer are preferred.

The term "enriched" is used herein to describe a compound having an enantiomeric purity greater than 1:1 in favour of the selected enantiomer. Compounds are preferred having a purity of about 1:3 or greater, e.g. 1:4. Particularly preferred are compounds having an enantiomeric purity of 1:9 or greater, such as 5:95 or 1:99.

Whereas some of the aforementioned compounds have been described in the literature, others have not, and are novel. Thus, the present invention provides in another aspect of the invention a compound of formula I

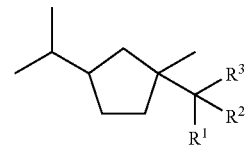

I wherein $R^1$ is hydrogen; or $R^1$ and $R^2$ are independently $C_{2-8}$ alkyl, $C_{2-8}$ alkenyl, $C_{3-8}$ cycloalkyl, $C_{3-8}$ cycloalkyl substituted with at least one $C_{1-3}$ alkyl, aryl, or aryl group substituted with at least one $C_{1-3}$ alkyl group; or $R^3$ is hydroxy, $C_{1-8}$ alkoxy, $C_{3-8}$ cycloalkoxy, $C_{2-5}$ alkoxymethyloxy, aryloxy, or aryloxy wherein the aromatic ring is substituted with $C_{1-3}$ alkyl; or $R^2$ and $R^3$ form together with the carbon atom to which they are attached a carbonyl group;

with the proviso that if $R^2$ and $R^3$ form together with the carbon atom to which they are attached a carbonyl group, then $R^1$ is not hydrogen or phenyl.

The compounds according to the present invention may be used alone or in combination with a base material. As used herein, the "base material" includes all known odourant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example, carrier materials, and other auxiliary agents commonly used in the art.

The following list comprises examples of known odourant molecules, which may be combined with the compounds of the present invention:

- ethereal oils and extracts, e.g. tree moss absolute, basil oil, castoreum, costus root oil, myrtle oil, oak moss absolute, geranium oil, jasmin absolute, patchouli oil, rose oil, sandalwood oil, wormwood oil, lavender oil or ylang-ylang oil;
- alcohols, e.g. citronellol, Ebanol™, eugenol, farnesol, geraniol, Super Muguet™, linalool, phenylethyl alcohol, Sandalore™, terpineol or Timberol™.
- aldehydes and ketones, e.g. α-amylcinnamaidehyde, Georgywood™, hydroxycitronellal, Iso E Super®, Isoraldeine®, Hedione®, maltol, Methyl cedryl ketone, methylionone or vanillin;
- ethers and acetals, e.g. Ambrox™, geranyl methyl ether, rose oxide or Spirambrene™.
- esters and lactones, e.g. benzyl acetate, Cedryl acetate, γ-decalactone, Helvetolide®, γ-undecalactone or Vetivenyl acetate.
- macrocycles, e.g. Ambrettolide, Ethylene brassylate or Exaltolide®.
- heterocycles, e.g. isobutylchinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odourant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in fine perfumery in amounts of from 0.1 to 20 weight percent, more preferably between 0.1 and 5 weight percent. However, these values are given only by way of example, since the experienced perfumer may also achieve effects or may create novel accords with lower or higher concentrations.

The compounds of the present invention may be employed into the fragrance application simply by directly mixing the fragrance composition with the fragrance application, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation of a compound of formula I or a compound of formula I enriched in one of their enantiomers, as a fragrance ingredient, either by directly admixing the compound to the application or by admixing a fragrance composition comprising a compound of formula I or a compound of formula I enriched in one of there enantiomers, which may then be mixed to a fragrance application, using conventional techniques and methods.

As used herein, "fragrance application" means any product, such as fine perfumery, e.g. perfume and eau de toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odourant. This list of products is given by way of illustration and is not to be regarded as being in any way limiting.

Compounds of formula I may be prepared for example by the Haller-Bauer rearrangement of fenchone (1,3,3-trimethyl-2-norbornanone) followed by hydrolysis to 3-isopropyl-1-methylcyclopentanecarboxylic acid under alkali conditions, e.g. in the presence of a base such as NaOH or KOH. The resulting acid will than be reacted with the corresponding alkyllithium product to give a compound of formula I wherein $R^2$ and $R^3$ form together with the carbon atom to which they are attached a carbonyl group. To give further compounds of the present invention the resulting ketone may be transformed to a secondary or tertiary alcohol either through reduction with e.g. $NaBH_4$ or by adding a Grignard reagent. To give even further compounds of the present invention, the resulting alcohol may further be transformed to the corresponding ether via Williamson reaction under conditions known in the art.

Optically pure compounds of formula I and enantiomeric mixtures of a compound of formula I enriched in one of the enantiomers, i.e. a compound of formula Ia or Ib, may be synthesised starting from optically pure fenchone or an enantiomeric mixture enriched in either (1R)-(−)-fenchone or (1S)-(+)-fenchone.

The invention is now further described with reference to the following non-limiting examples.

All end products described in the following Examples 1 to 8 are colourless oils. They were obtained starting from (1R)-(−)- and (1S)-(+)-fenchone that contained 8% and 2% respectively of the other enantiomer. The reported NMR data were measured under the following general conditions: $^1H$ at 400 and $^{13}C$ at 100 MHz; in $CDCl_3$; chemical shifts (δ) in ppm downfield from TMS; coupling constants J in Hz.

EXAMPLE 1

(1R,cis)-1-Ethoxymethoxymethyl-3-isopropyl-1-methylcyclopentane a)

[(1R,cis)3-isopropyl-1-methylcyclopentyl]methanol

A solution of (1R,cis)-3-Isopropyl-1-methylcyclopentanecarboxylic acid (70.0 g, 0.41 mol), obtained from (1R)-(−)-fenchone (V. Braun, J.; Jacob, A. *Chem. Ber.* 1933, 66, 1461) in diethyl ether (100 ml) was slowly added, under nitrogen, to a suspension of lithium aluminium hydride (13.3 g, 0.35 mol) in the same solvent (500 ml). After heating at reflux during 3 h, the reaction mixture was cooled down to 10° C., 2N NaOH solution (70 ml) was carefully added and stirring continued for 0.5 h. The white solid was filtered off, the filtrate washed with brine (2×500 ml), dried (MgSO$_4$) and concentrated in vacuo. The crude product (79.0 g) was purified by distillation using a 10 cm Vigreux column (0.9-1.1 mbar), 96-98° C.) to give [(1R,cis)-3-isopropyl-1-methylcyclopentyl]methanol (57.0 g, 90% yield).

b) (1R,cis)-1-Ethoxymethoxymethyl-3-isopropyl-1-methylcyclopentane

A solution of [(R,cis)-3-isopropyl-1-methylcyclopentyl]methanol (3.9 g 19 mmol) from Example 1 in THF (20 ml) was added to a suspension of sodium hydride (0.77 g, 32 mmol) in the same solvent (120 ml). After stirring at reflux overnight, chloromethyl ethyl ether (3.8 ml, 38.5 mmol) was added and stirring at reflux continued for 2 h. The cooled reaction mixture was treated with 2N HCl (100 ml) and extracted with MTBE (2×100 ml). The organic filtrate was washed with brine (2×50 ml), dried (MgSO$_4$) and concentrated in vacuo. The crude [(1R,cis)-1-ethoxymethoxymethyl-3-isopropyl-1-methylcyclopentane (4.0 g) was purified by bulb-to-bulb distillation (3.25 g, 79% yield).

$^1$H-NMR: δ0.86 (d, J=6.7, 3H), 0.88 (d, J=6.7, 3H), 1.02 (s, 3H), 1.12 (dd, J=12.3, 11.0, 1H), 1.16-1.38 (m, 3H), 1.22 (t, J=7.0, 3H), 1.50 (dd, J=12.5, 6.6, 1H), 1.56-1.71 (m, 2H), 1.75-1.86 (m, 1H), 3.28 (q, J=8.8, 1H), 3.58 (d, J$_{AB}$=7.1, 1H), 3.62 (d, J$_{AB}$=7.1, 1H), 4.68 (s, 3H). $^{13}$C NMR: δ 15.0 (q), 21.4 (2q), 25.5 (q), 30.2 (t), 33.7 (d), 36.2 (t), 41.9 (t), 42.5 (s), 46.7 (d), 62.8 (t), 77.1 (t), 95.2 (t). [α]$_D^{22}$–10.5 (c 1.0, EtOH).

Odour description: fruity, green, floral, hesperidic.

EXAMPLE 2

1-[(1R,cis)-3-Isopropyl-1-methylcyclopentyl]propan-1-one

A 0.5M solution of ethyllithium in diethyl ether (150 ml, 75 mmol) was added dropwise during 6 h into a solution of (1R,cis)-3-isopropyl-1-methylcyclopentanecarboxylic acid (4.0 g, 24 mmol) in the same solvent (40 ml) at 10° C. The reaction mixture was poured on ice-cold aqueous NH$_4$Cl solution (200 ml) and extracted with MTBE (2×150 ml). The combined organic phases were washed with 2N NaOH solution (100 ml) and brine (2×100 ml), dried (MgSO$_4$) and concentrated in vacuo. The crude product (3.1 g) was purified by flash chromatography (silica gel, n-hexane/MTBE 16:1) to give 1-[(1R,cis)-3-isopropyl-1-methylcyclopentyl]propan-1-one (1.15 g, 27% yield).

$^1$H-NMR: δ0.88 (2d, J=6.6, 6H), 1.05 (t, J=7.3, 3H), 1.20 (s, 3H), 1.23 (dq, J=12.5, 9.2, 1H), 1.33-1.43 (m, 2H), 1.56-1.76 (m, 3H), 1.80-1.89 (m, 1H), 2.08 (ddd, J=13.1, 9.1, 4.1, 1H), 2.50 (q, J=7.3, 2H). $^{13}$C-NMR: δ8.5 (q), 21.5 (2q), 25.2 (q), 30.3 (t), 30.4 (t), 33.5 (d), 35.8 (t), 41.3 (t), 46.6 (d), 55.2 (s), 215.8 (s). [α]$_D^{22}$–3.5 (c 1.1, EtOH).

Odour description: green, earthy/mossy, fruity, floral.

EXAMPLE 3

The following compounds were prepared according to the general procedure described in Example 2.

A) 1-[(1S,cis)-3-Isopropyl-1-methylcyclopentyl]propan-1-one

[α]$_D^{22}$+4.0 (c 0.9, EtOH).
Odour description: earthy/mossy, fruity, green.

B) 1-[(1R,cis)-3-Isopropyl-1-methylcyclopentyl]pentan-1-one $^1$H-NMR: δ0.88 (2d, J=6.5, 6H), 0.91 (t, J=7.3, 3H), 1.19 (s, 3H), 1.23 (dq, J=12.4, 9.1, 1H), 1.26-1.43 (m, 4H), 1.52-1.76 (m, 5H), 1.80-1.88 (m, 1H), 2.08 (ddd, J=13.1, 9.2, 4.0, 1H), 2.46 (t, J=7.1, 2H). $^{13}$C-NMR: δ13.9 (q), 21.5 (2q), 22.5 (t), 25.1 (q), 26.4 (t), 30.3 (t), 33.5 (d), 35.7 (t), 37.1 (t), 41.1 (t), 46.7 (d), 55.3 (s), 215.2 (s), [α]$_D^{22}$–4.5 (c 1.0, EtOH).

Odour description: green, floral.

EXAMPLE 4

1-[(1R,cis)-3-Isopropyl-1-methylcyclopentyl]propan-1-ol

A solution of 1-[(1R,cis)-3-isopropyl-1-methylcyclopentyl]propan-1-one (0.8 g, 4.4 mmol) in ethanol (5 ml) was added to a cold (ice-bath) solution of sodium borohydride (0.4 g, 10 mmol) in the same solvent (17 ml). After 4.5 h stirring at room temperature, the reaction mixture was poured on ice-cold 2M HCl (50 ml) and extracted with MTBE (2×100 ml). The combined organic phases were washed with brine (2×100 ml), dried (MgSO$_4$) and concentrated in vacuo. The crude product (1.1 g) was purified by flash chromatography (silica gel, n-hexane/MTBE 10:1) to give 1-[(1R,cis)-3-isopropyl-1-methylcyclopentyl]propan-1-ol (0.53 g, 66% yield, diastereoisomer ratio ~1:1). $^1$H-NMR δ: 0.86 (d, J=6.6, 3H), 0.87 (d, J=6.6, 3H), 0.88 (2d, J=6.6, 6H), 0.91 (s, 3H), 0.92 (s, 3H), 1.00 (t, J=7.4, 3H), 1.01 (t, J=7.3, 3H), 1.04 (t, J=11.5, 1H), 1.13 (t, J=11.5, 1H), 1.16-1.74 (m, 17H), 1.41 (dd, J=12.1, 6.6, 1H), 1.77-1.88 (m, 2H), 3.16 (dd, J=10.3, 1.8, 1H), 3.18 (dd, J=10.3, 1.8, 1H). $^{13}$C-NMR: δ611.4 (2q), 21.4 (5q), 21.6 (1q), 25.2 (t), 25.3 (t), 29.7 (t), 29.9 (t), 33.7 (2), 36.0 (t), 36.4 (t), 42.2 (t), 42.4 (t), 46.1 (d), 46.2 (d), 46.9 (s), 47.0 (s), 81.8 (d), 82.2 (d). [α]$_D^{22}$–7.5 (c 1.0, EtOH).

Odour description: anisic, floral, green, marine.

EXAMPLE 5

The following compounds were prepared according to the general procedure described in Example 4.

A) 1-[(1S,cis)-3-Isopropyl-1-methylcyclopentyl]propan-1-ol

[α]$_D^{22}$+11.0 (c 1.1, EtOH).
Odour description: fruity, green, leathery, floral.

B) 1-[(1R,cis)-3-Isopropyl-1-methylcyclopentyl]butan-1-ol

Diastereoisomer ratio ~1:1.
$^1$H-NMR: δ0.87 (d, J=6.6, 3H), 0.875 (d, J=6.6, 3H), 0.88 (2d, J=6.6, 6H), 0.91 (s, 3H), 0.92 (s, 3H), 0.935 (t, J=7.2, 3H), 0.94 (t, J=7.2, 3H), 1.03 (t, J=11.6, 1H), 1.12 (t, J=11.6, 1H), 1.16-1.75 (m, 22H), 1.77-1.88 (m, 2H), 3.27 (m, 2H). $^{13}$C-NMR: δ14.0 (2q), 20.0 (2t), 21.4 (5q), 21.6 (q), 29.7 (t), 29.9 (t), 33.7 (2d), 34.6 (t), 34.7 (t), 36.0 (t), 36.4 (t), 42.2 (t), 42.4 (t), 46.2 (d), 46.3 (d), 46.8 (s), 46.9 (s), 79.8 (d), 80.1 (d). [α]$_D^{22}$–6.5 (c 1.0, EtOH).

Odour description: green, spicy, fruity.

C) 1-[(1R,cis)-3-Isopropyl-1-methylcyclopentyl]pentan-1-ol

Diastereoisomer ratio ~1:1.

$^1$H-NMR: δ0.87 (d, J=6.6, 3H), 0.875 (d, J=6.6, 3H), 0.88 (2d, J=6.6, 6H), 0.91 (t, J=7.2, 3H), 0.91 (s, 3H), 0.915 (t, J=7.2, 3H), 0.92 (s, 3H), 1.02 (t, J=11.6, 1H), 1.12 (t, J=11.6, 1H), 1.16-1.75 (m, 26H), 1.77-1.87 (m, 2H), 3.25 (dd, J=9.6, 1.8, 1H), 3.26 (dd, J=9.6, 1.8, 1H). $^{13}$C-NMR: δ14.1 (2q), 21.5 (4q), 21.6 (q), 21.7 (q), 22.8 (2t), 29.2 (t), 29.3 (t), 29.8 (t), 30.0 (t), 32.3 (t), 32.4 (t), 33.8 (d), 33.9 (d), 36.1 (t), 36.5 (t), 42.3 (t), 42.6 (t), 46.3 (d), 46.4 (d), 47.0 (s), 47.1 (s), 80.2 (d), 80.5 (d). $[α]_D^{22}$−9.0 (c 1.0, EtOH).

Odour description: green, fruity.

EXAMPLE 6

2-[(1R,cis)-3-Isopropyl-1-methylcyclopentyl]propan-2-ol a) 1-[(1R,cis)-3-Isopropyl-1-methylcyclopentyl]ethanone A 1.6M solution of methyllithium in diethyl ether (200 ml, 0.32 mol) was added dropwise during 25 min. into a solution of (1R,cis)-3-Isopropyl-1-methylcyclopentanecarboxylic acid (25.5 g, 0.15 mol) in THF (250 ml) at 0° C. After stirring at 0° C. for 3 h, chlorotrimethylsilane (151 ml, 1.2 mol) was added with cooling and the reaction mixture was allowed to warm up to room temperature, poured on ice-cold water (200 ml), stirred for 0.5 h and extracted with MTBE (2×250 ml). The combined organic phases were washed with water (200 ml), 2M NaOH (150 ml) and brine (3×200 ml), dried (MgSO$_4$) and concentrated in vacuo to give the crude 1-[(1R, cis)-3-isopropyl-1-methylcyclopentyl]ethanone (27.6 g), a sample of which (1.5 g) was purified by bulb-to-bulb distillation (0.93 g, 68% yield).

b) 2-[(1R,cis)-3-Isopropyl-1-methylcyclopentyl] propan-2-ol

1-[(1R,cis)-3-Isopropyl-1-methylcyclopentyl]ethanone (3.0 g, 18 mmol) in diethyl ether (10 ml) was added to a 3M solution of methylmagnesium bromide in diethyl ether (7.5 ml, 22.5 mmol) diluted with the same solvent (20 ml) at 0° C., under nitrogen. The reaction mixture was stirred at room temperature for 1.5 h, poured on an ice-cold NH$_4$Cl solution (100 ml) and extracted with MTBE (2×100 ml). The combined organic layers were washed with brine (2×50 ml), dried (MgSO$_4$) and concentrated in vacuo. The crude product (2.92 g) was purified by bulb-to-bulb distillation (2.88 g, 88% yield).

$^1$H-NMR: δ0.88 (d, J=6.7, 3H), 0.89 (d, J=6.7, 3H), 0.99 (s, 3H), 1.12-1.24 (m, 2H), 1.19 (2s, 6H), 1.31 (s, 1H), 1.32-1.41 (m, 3H), 1.64 (m, 1H), 1.79-1.90 (m, 2H). $^{13}$C-NMR: δ21.45 (q), 21.5 (q), 24.8 (q), 25.7 (q), 25.9 (q), 30.8 (t) 33.6 (d), 33.9 (t), 40.0 (t), 46.6 (d), 49.7 (s), 74.8 (s). $[α]_D^{22}$−12.5 (c 0.7, EtOH).

Odour description: earthy/mossy, woody, camphoraceous, ambery, sweet.

EXAMPLE 7

The following compounds were prepared according to the general procedure described in Example 6.

A) 2-[(1S,cis)-3-Isopropyl-1-methylcyclopentyl] propan-2-ol $[α]_D^{22}$+15.0 (c 1.1, EtOH).

Odour description: hesperidic/citrus, fruity, fresh (grapefruit).

B) 2-[(1S,cis)-3-Isopropyl-1-methylcyclopentyl] butan-2-ol

Diastereoisomer ratio ~1:1.
$^1$H-NMR: δ0.88 (d, J=6.6, 3H), 0.885 (3d, J=6.6, 9H), 0.93 (2t, J=7.3, 6H), 0.97 (2s, 6H), 1.07-1.56 (m, 14H), 1.09 (2s, 6H), 1.51 (t, J=7.6, 2H), 1.55-1.68 (m, 2H), 1.78-1.94 (m, 4H). $^{13}$C-NMR: δ7.8 (2q), 21.0 (q), 21.2 (q), 21.5 (4q), 24.7 (2q), 29.2 (t), 29.3 (t), 30.6 (t), 30.7 (t), 33.6 (2d), 33.7 (t), 34.0 (t), 39.6 (t), 40.2 (t), 46.2 (d), 46.4 (d), 50.4 (s), 50.5 (s), 76.2 (s), 76.3 (s). $[α]_d^{22}$−15.0 (c 1.0, EtOH).

Odour description: camphoraceous, earthy/mossy, woody, slightly patchouli.

C) 2-[(1S,cis)-3-Isopropyl-1-methylcyclopentyl] butan-2-ol $[α]_D^{22}$+17.5 (c 1.0, EtOH).
Odour: fruity, floral, green (pineapple).

D) 2-[(1R,cis)-3-Isopropyl-1-methylcyclopentyl] pent-3-en-2-ol

Diastereoisomer ratio ~1:1.
$^1$H-NMR: δ0.87 (d, J=6.6, 3H), 0.88 (3d, J=6.6, 9H), 0.97 (2s, 6H), 1.09-1.22 (m, 4H), 1.23 (2s, 6H), 1.31-1.46 (m, 8H), 1.55-1.67 (m, 2H), 1.71 (2m, 6H), 1.75-1.94 (m, 4H), 5.62-5.67 (m, 4H). $^{13}$C-NMR: 517.7 (2q), 21.4 (q), 21.5 (3q), 23.9 (2q), 24.8 (q), 24.9 (q), 30.8 (t), 30.9 (t), 33.5 (d), 33.6 (d), 34.0 (t), 34.1 (t), 40.0 (t), 40.1 (t), 46.4 (d), 46.5 (d), 49.3 (2s), 76.5 (s), 76.6 (s), 123.0 (d), 123.1 (d), 136.3 (d), 136.5 (d). $[α]_D^{22}$−13.0 (c 1.0, EtOH).

Odour description: earthy/mossy, woody, mushroom.

EXAMPLE 8

3-[(1R,cis)-3-Isopropyl-1-methylcyclopentyl]pentan-3-ol

Prepared according to the general procedure described in Example 6 using 4.3 mol. equivalents of ethyllithium. Purified by flash chromatography (n-hexane/MTBE 15:4). Yield 26%.

$^1$H-NMR: δ0.86 (2d, J=6.7, 6H), 0.91 (t, J=7.5, 6H), 1.00 (s, 3H), 1.11-1.23 (m, 3H), 1.30-1.44 (m, 3H), 1.48-1.68 (m, 5H), 1.76-1.96 (m, 2H). $^{13}$C-NMR: δ9.1 (q), 21.6 (q), 21.7 (q), 24.9 (q), 27.7 (t) 28.1 (t), 30.8 (t), 33.8 (d), 34.8 (t), 40.8 (t), 46.1 (d), 51.0 (s), 77.5 (s). $[α]_D^{22}$−8.0 (c 0.5, EtOH).

Odour description: green, fatty, floral.

The invention claimed is:
1. A fragrance composition comprising a compound of the following formula,

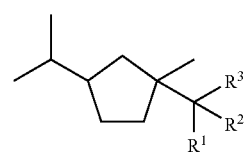

I wherein
R$^1$ is hydrogen; or $R^1$ and $R^2$ are independently $C_{2-8}$ alkyl, $C_{2-8}$ alkenyl, $C_{3-8}$ cycloalkyl, $C_{3-8}$ cycloalkyl substituted with at least one $C_{1-3}$ alkyl, aryl, or aryl group substituted with at least one $C_{1-3}$ alkyl group;

$R^3$ is hydroxy, $C_{1-8}$ alkoxy, $C_{3-8}$ cycloalkoxy, $C_{2-5}$ alkoxymethyloxy, aryloxy, or aryloxy wherein the aromatic ring is substituted with $C_{1-3}$ alkyl; or $R^2$ and $R^3$ form together with the carbon atom to which they are attached a carbonyl group.

2. A fragrance composition according to claim 1 wherein the compound of formula I is enriched in one of its enantiomers of formula Ia or formula Ib

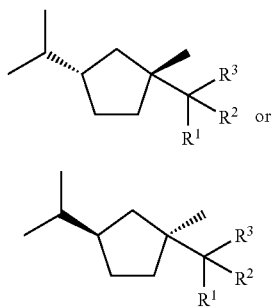

wherein $R^1$, $R^2$ and $R^3$ have the same meaning as given in claim 1.

3. A fragrance composition according to claim 1 comprising a compound selected from:
(1R,cis)-1-ethoxymethoxymethyl-3-isopropyl-1-methyl-cyclopentane,
1-[(1R,cis)-3-isopropyl-1-methylcyclopentyl]propan-1-one,
1-[(1S,cis)-3-isopropyl-1-methylcyclopentyl]propan-1-one,
1-[(1R,cis)-3-isopropyl-1-methylcyclopentyl]pentan-1-one,
1-[(1R,cis)-3-isopropyl-1-methylcyclopentyl]propan-1-ol,
1-[(1S,cis)-3-isopropyl-1-methylcyclopentyl]propan-1-ol,
1-[(1R,cis)-3-isopropyl-1-methylcyclopentyl]pentan-1-ol,
2-[(1R,cis)-3-isopropyl-1-methylcyclopentyl]propan-2-ol,
2-[(1S,cis)-3-isopropyl-1-methylcyclopentyl]propan-2-ol,
2-[(1R,cis)-3-isopropyl-1-methylcyclopentyl]butan-2-ol,
2-[(1S,cis)-3-isopropyl-1-methylcyclopentyl]butan-2-ol,
2-[(1R,cis)-3-isopropyl-1-methylcyclopentyl]pent-3-en-2-ol,
3-[(1R,cis)-3-isopropyl-1-methylcyclopentyl]pentan-3-ol, and
1-[(1R,cis)-3-isopropyl-1-methylcyclopentyl]butan-1-ol.

4. A fragrance application comprising a fragrance composition according to claim 1.

5. A fragrance application according to claim 4 wherein the fragrance application is selected from: a perfume, household product, laundry product, body care product or cosmetic product.

6. A method of manufacturing a fragrance application, comprising the step of incorporating into the fragrance application a fragrance composition according to claim 1.

7. A compound of formula I

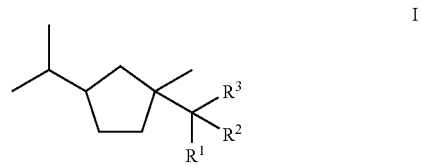

wherein
$R^1$ is hydrogen; or
$R^1$ and $R^2$ are independently $C_2$ alkyl, $C_{2-8}$ alkenyl, $C_{3-8}$ cycloalkyl, $C_{3-8}$ cycloalkyl substituted with at least one $C_{1-3}$ alkyl, aryl, or aryl group substituted with at least one $C_{1-3}$ alkyl group;
$R^3$ is hydroxy, $C_{1-8}$ alkoxy, $C_{3-8}$ cycloalkoxy, $C_{2-5}$ alkoxymethyloxy, aryloxy, or aryloxy wherein the aromatic ring is substituted with $C_{1-3}$ alkyl; or
$R^2$ and $R^3$ form together with the carbon atom to which they are attached a carbonyl group;
with the proviso that if $R^2$ and $R^3$ form together with the carbon atom to which they are attached a carbonyl group, then $R^1$ is not hydrogen or phenyl.

8. A fragrancing composition comprising one or more compounds selected from:
(1R,cis)-1-ethoxymethoxymethyl-3-isopropyl-1-methyl-cyclopentane,
1-[(1R,cis)-3-isopropyl-1-methylcyclopentyl]propan-1-one,
1-[(1S,cis)-3-isopropyl-1-methylcyclopentyl]propan-1-one,
1-[(1R,cis)-3-isopropyl-1-methylcyclopentyl]pentan-1-one,
1-[(1R,cis)-3-isopropyl-1-methylcyclopentyl]propan-1-ol,
1-[(1S,cis)-3-isopropyl-1-methylcyclopentyl]propan-1-ol,
1-[(1R,cis)-3-isopropyl-1-methylcyclopentyl]pentan-1-ol,
2-[(1R,cis)-3-isopropyl-1-methylcyclopentyl]propan-2-ol,
2-[(1S,cis)-3-isopropyl-1-methylcyclopentyl]propan-2-ol,
2-[(1R,cis)-3-isopropyl-1-methylcyclopentyl]butan-2-ol,
2-[(1S,cis)-3-isopropyl-1-methylcyclopentyl]butan-2-ol,
2-[(1R,cis)-3-isopropyl-1-methylcyclopentyl]pent-3-en-2-ol,3-[(1R,cis)-3-isopropyl-1-methylcyclopentyl)pentan-3-ol, and
1-[(1R,cis)-3-isopropyl-1-methylcyclopentyl]butan-1-ol.

* * * * *